US008463005B2

(12) United States Patent
Erbel et al.

(10) Patent No.: US 8,463,005 B2
(45) Date of Patent: Jun. 11, 2013

(54) STENT AND METHOD FOR DETERMINING THE POSITION OF A STENT

(75) Inventors: Stephan Erbel, München (DE); Verena Schultheis, München (DE); Rainer Birkenbach, Erding (DE)

(73) Assignee: Brainlab AG, Feldkirchen (DE)

( * ) Notice: Subject to any disclaimer, the term of this patent is extended or adjusted under 35 U.S.C. 154(b) by 954 days.

(21) Appl. No.: 12/396,658

(22) Filed: Mar. 3, 2009

(65) Prior Publication Data

US 2010/0228340 A1    Sep. 9, 2010

(51) Int. Cl.
*G06K 9/00*      (2006.01)
(52) U.S. Cl.
USPC .......................................................... 382/128
(58) Field of Classification Search
None
See application file for complete search history.

(56) References Cited

U.S. PATENT DOCUMENTS

| | | | | |
|---|---|---|---|---|
| 7,366,562 | B2 * | 4/2008 | Dukesherer et al. | 600/424 |
| 7,620,221 | B2 * | 11/2009 | Florent et al. | 382/128 |
| 7,697,972 | B2 * | 4/2010 | Verard et al. | 600/424 |
| 7,764,984 | B2 * | 7/2010 | Desmedt et al. | 600/424 |
| 8,046,052 | B2 * | 10/2011 | Verard et al. | 600/424 |
| 8,359,730 | B2 * | 1/2013 | Burg et al. | 29/606 |
| 2002/0095081 | A1 * | 7/2002 | Vilsmeier | 600/407 |
| 2005/0220468 | A1 * | 10/2005 | Kitajima | 399/48 |
| 2006/0023840 | A1 * | 2/2006 | Boese | 378/98.12 |
| 2006/0058638 | A1 * | 3/2006 | Boese et al. | 600/411 |

OTHER PUBLICATIONS

J. Carl et al., Medical Physics, 33 (12), 2006, pp. 4600-4605.

* cited by examiner

*Primary Examiner* — Nancy Bitar
(74) *Attorney, Agent, or Firm* — Renner, Otto, Boisselle & Sklar, LLP

(57) ABSTRACT

A method for determining the position of a stent within a body, comprising the steps of:
  providing a 3D dataset of voxels representing a 3D image containing the stent;
  determining a starting position for the determination of the stent position;
  determining the axis of symmetry of the stent in the 3D dataset;
  determining a second dataset representing at least one image containing the stent in its present position; and
  determining the positional offset of the stent by image fusion using the 3D dataset and the second dataset and by penalizing a rotation around the axis of symmetry as compared to the starting position.

23 Claims, 4 Drawing Sheets

STENT AND METHOD FOR DETERMINING THE POSITION OF A STENT

Figure 1:
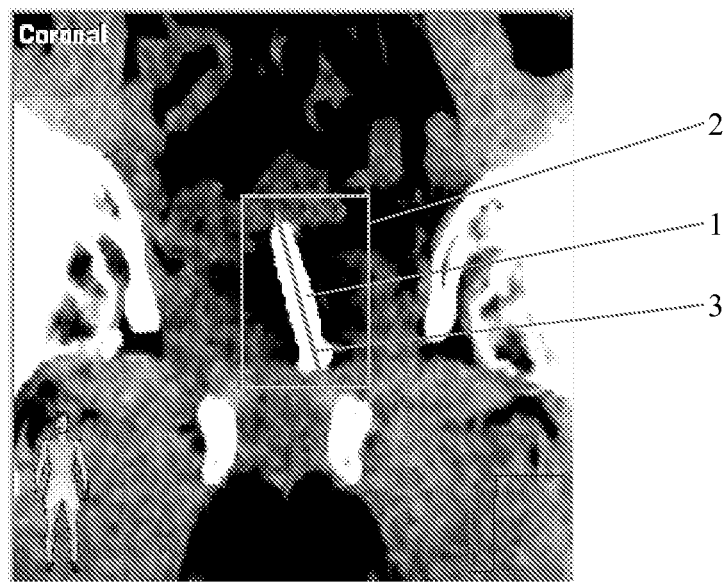

The present invention relates to the field of identifying and localizing a stent which is placed within a body.

It is often necessary to know the exact position of an anatomical structure within a body. Examples of an anatomical structure are bones, organs or tumors. If the anatomical structure is a tumor, it is essential to know the exact position of the tumor in order to align the patient with the isocenter of a linear accelerator, in order to irradiate the tumor as radiotherapy.

In the treatment of prostate cancer, for example, problems arise due to respiration or the movement of the bladder or rectum. Therefore, methods for visualizing the position of the prostate are needed.

In order to locate the anatomical structure, fiducial markers are sometimes implanted, in order to visualize the target in x-ray images. More recently, stent-type markers have been used which have substantial intrinsic advantages over other types of marker. For example, stent-type markers can be non-surgically placed into body cavities such as the urethra or bronchi.

In a new but already clinically used procedure, cylindrical metallic stents are inserted into the prostatic urethra in order to indirectly visualize the position of the prostate. This procedure has several advantages over the commonly used implanted markers: the stents can be relatively easily inserted and removed; and side effects, such as the transfer of tumor tissue to the healthy tissue surrounding the tumor, are avoided.

In Medical Physics, 33 (12), 2006, pages 4600 to 4605, J. Carl et al. describe a geometry-based detection algorithm for x-ray images of stents. A digital reconstructed radiograph (DRR) is used to determine the direction of the stent axis in images obtained from electronic portal image devices (EPIDs). These EPID images are rotated in such a way that the stent axis is approximately vertical. Several image processing steps, such as line enhancement and the detection of pixels which are the stent diameter apart from each other, are then performed on the EPID images, in order to detect the stent in the 2-dimensional EPID images. In order to use this information for patient positioning in the field of radiotherapy, it is necessary to compare the position of the stents in the EPID images (or any other type of 2D- or 3D-images used as secondary dataset) with their reference position in the 3-dimensional datasets that are used to define the geometry and relative location of the treatment volumes. This publication does not teach any method to determine or measure the position in the 3-dimensional dataset. It is thus not possible to derive a necessary correction to the patients position from the knowledge of the stent position in the 2-dimensional images. Though it is theoretically imaginable to manually try to define the geometry of the stent in the 3D dataset such a procedure would be time consuming, and operator dependent. As the main axis of the stents will typically not be aligned with any major axis, it is especially complicated to define characteristic points that describe the geometry and location of the stent. Any operator variability in this task will directly influence the treatment accuracy.

It is the object of the present invention to improve and simplify the determination of the position of a stent which is placed within a body. Throughout this document, the term "position" is understood to mean a combination of location and orientation, wherein "location" indicates the translational location in space and "orientation" means the rotational alignment, preferably about three axes.

A first aspect of the present invention relates to a method for determining the position of a stent which is placed within a body. The method comprises the steps of: providing a 3D dataset of voxels representing a 3D image containing the stent; determining a starting position for the determination of the stent position; determining the axis of symmetry of the stent in the 3D dataset; determining a second dataset representing at least one image containing the stent in its present position; and determining the position of the stent by image fusion using the 3D dataset and the second dataset, wherein a rotation around the axis of symmetry versus the starting position is penalized.

The 3D dataset, which is also called first 3D dataset, consists of a multitude of voxels and represents a 3D image containing the stent. For example, each voxel has a grey value. The grey value may represent the density of a material in a predetermined volume element. The 3D dataset can be generated for example by a computer tomograph or magnetic resonance imaging. The volume covered by the 3D dataset fully contains the stent.

The position of the stent can be an absolute position, for example versus a reference like the apparatus which carries out the method, the apparatus generating the image contained in the second dataset or a reference coordinate system. Alternatively, the position of the stent can be a relative position. For example, a nominal position is defined for the 3D dataset and the position of the stent is a relative position versus the stent position in the 3D dataset in the 3D dataset's nominal position. The (relative) position of the stent therefore equals the translational and rotational offset which has to be applied to the 3D dataset from its nominal position to match the stent in its current position. The nominal position of the 3D dataset is for example a position which corresponds to the position of the body in which the structure within the body is aligned with the isocenter of the linear accelerator.

The starting position is a position which is supposed to be close to the actual position of the stent.

In one embodiment of the present invention, a nominal position is defined for the 3D dataset and the starting position for the determination of the stent position is the stent position in the 3D dataset in the 3D dataset's nominal position. In another embodiment, the starting position is determined from a pre-registration. During pre-registration, the position of the body is determined, for example using at least one marker placed on the body or using image fusion to align the body within which the stent is comprised.

The marker can be an external marker device attached to the body. The stent is placed elastically/half-rigidly embedded into the body at a predetermined location, resulting in prior knowledge of the approximate position of the stent as compared to the body and therefore the marker devices. Due to deformation of the body, this starting position is of limited accuracy and a more exact measurement of its position is thus beneficial for radiotherapy positions.

A marker device can be a reference star, a pointer and/or one or more markers.

It is the object of a marker to be detected by a marker detection device (for example, a camera or an ultrasound receiver), such that its spatial location (i.e. its position and/or alignment) can be ascertained. Such markers can be active markers. An active marker emits for example electromagnetic radiation and/or waves, wherein said radiation can be in the infrared, visible and/or ultraviolet spectral range. However, the marker can also be passive, i.e. it can reflect for example electromagnetic radiation of the infrared, visible and/or ultraviolet spectral range. To this end, the marker can be provided with a surface which has corresponding reflective properties.

It is also possible for a marker to reflect and/or emit electromagnetic radiation and/or waves in the radio frequency range or at ultrasound wavelengths. A marker preferably has a spherical and/or spheroid shape and may therefore be referred to as a marker sphere; markers can also, however, exhibit a cornered—for example, cube-shaped—shape.

Image fusion for determining the starting position may be based on anatomical structures such as for example bones. The result of image fusion is the position of the anatomical structure, for example the bone. Preferably, this anatomical structure is not the anatomical structure to be localized using the stent. Since the position of the stent as compared to the bone is approximately known, the position of the stent is also approximately known, and this is used as the starting position.

Another option is to determine the starting position as the calculated position of the stent in a previous stent position determination iteration, i.e. the method as explained above is used to determine the position of the stent, and this calculated position is used as the starting position in a subsequent execution of the method. This is particularly useful if the position of the stent is to be tracked over time.

In an alternative embodiment, a nominal position is defined for the 3D dataset and the starting position is determined from the stent position in the 3D dataset in the 3D dataset's nominal position and a pre-registration. In this embodiment, for example, the three translational dimensions and the two rotational dimensions which are not around the stent's axis of symmetry are used for the starting position. The starting position with regards to the stent's axis of symmetry is derived from the pre-registration.

The axis of symmetry of the stent can be determined in the 3D dataset in different ways. One example is explained in detail below.

The at least one image represented by the second dataset can be a 2D image or a 3D image. A 2D image is for example an x-ray image, the 3D image is for example a 3D tomographic scan of the body or of a part of the body. If the image is a 2D image, 3D to 2D image fusion is used for determining the position of the stent. This kind of image fusion can be performed for example by x-ray to DRR fusion. One of many algorithms that may be used for this fusion operation is a signed gradient correlation algorithm. If the image is a 3D image, 3D to 3D image fusion is used for determining the position of the stent. This kind of image fusion can be performed by a 3D to 3D correlation of two 3D-image datasets, using algorithms such as for instance a mutual information correlation algorithm. The term "image registration" is also alternatively used to describe this same process. If the image is a 3D image, the second dataset is also called second 3D dataset.

During 3D to 2D image fusion, which is a method well-known to the person skilled in the art, an actual x-ray image is taken and a set of virtual x-ray images (also called DRR images) of a three-dimensional object is created. Each virtual x-ray image is based on a different virtual position of the object, wherein the viewing direction of the DRR images equals the viewing direction of the actual x-ray image. Each virtual x-ray image is in turn compared to the actual x-ray image, and the virtual image resulting in the best match is chosen. The best match may be identified using a measure of similarity. Using an optimization algorithm, new sets of DRR images might be dynamically created for positions in the vicinity of previously created DRRs that have resulted in a good match values.

To achieve an optimal match result it is beneficial to include an optimization of rotational parameters. As stent markers are typically substantially cylindrical objects that can be nearly symmetrical around their main axis, a rotation around this axis has little influence on the appearance of the created DRRs. This can result in arbitrary rotations of the fusion around this main axis, which are not representative of the real rotational position of the stent. Such rotations can lead to inappropriate fusion results, where only the points substantially on the main axis are properly fused whereas all other points of the 3D dataset are rotated out of the correct registration position.

During 3D to 3D image fusion, which is also a method well-known to the person skilled in the art, the first and second 3D dataset are virtually moved into different respective positions and their similarity is measured based on techniques such as gradient correlation or mutual information correlation. Using an optimizer, the relative positions of the two datasets is modified to determine the position that results in the best similarity value. A typical example for second 3D datasets are Cone-Beam CT datasets that can be acquired e.g. using imaging systems built into or attached to commercially available linear accelerator systems.

For the reasons given above, symmetry of the stent can impair the result of the image fusion. In accordance with the present invention this problem is solved by using two criteria for identifying the best match: the similarity between the first and second datasets for a given virtual position of the first 3D dataset; and the rotational deviation of the stent (for that same position) around its axis of symmetry versus the starting position.

Penalizing the rotation can be an integral part of the image fusion step or a separate step. For example, if it is an integral part, the rotational deviation can be part of the measure of similarity within the image fusion process. Penalizing may be implemented by subtracting a penalty factor from the original measure of similarity or by dividing the original measure of similarity by the penalty factor. The resulting measure of similarity for a current virtual position of first 3D dataset (and therefore the position of the stent) is then compared to the measure of similarity of the best match thus far. If the current virtual position of the first 3D dataset results in a better match than the best match thus far, the position of the best match is changed to that of said current virtual position. This only requires a low memory capacity, because only the position and the measure of similarity of the best match are stored, for comparison purposes.

If the rotation is penalized in a step which is separate from image fusion, then image fusion creates a set of measures of similarity corresponding to a set of virtual positions of the first 3D dataset (and therefore the virtual positions of the stent). In this case, the measure of similarity is only based on the similarity between a virtual x-ray image and the actual x-ray image, or the similarity between the first and second 3D datasets. The penalty for the rotation around the axis of symmetry is then applied to the measures of similarity in a second step. This allows the penalty to be modified without having to perform image fusion again.

Preferably, the penalty for the rotation around the axis of symmetry increases as the deviation from the starting position increases. The increase in the penalty can for example be linear, quadratic, exponential or of inverse Gaussian distribution.

One way of determining the axis of symmetry includes the steps of: applying a threshold to the voxels in the 3D dataset; determining the center of mass and the tensor of inertia of the thresholded voxels; and calculating the axis of symmetry from the center of mass and the tensor of inertia. By applying the threshold, the voxels having a low grey value are omitted, for example by setting the grey value for each voxel below the threshold to zero. Since a stent is typically made of a material exhibiting a high density, thus resulting in large grey values, applying the threshold isolates the stent from the rest of the image data. Optionally, applying the threshold can include a binarizing step in which the grey values of all voxels which are equal to or greater than the threshold value are set to the maximum possible grey value.

Methods for calculating the center of mass of an object are well-known in the prior art. The tensor of inertia combines the moments of inertia of the stent around different axes, preferably three axes which are perpendicular to each other. In one example embodiment, the axis of symmetry is calculated as the tensor's eigenvector associated with the smallest eigenvalue of the tensor.

Optionally, the axis of symmetry is plotted in the 3D dataset, and the 3D dataset is displayed together with the axis of symmetry. This allows an operator to judge whether the determination of the axis of symmetry is feasible.

When determining the axis of symmetry of the stent, the region of voxels within the 3D dataset can also optionally be constrained, i.e. not all but only some of the voxels in the 3D dataset are used for determining the axis of symmetry. This allows the exclusion of voxels which would impair the determination of the axis of symmetry, for example voxels which exhibit a high grey value but do not belong to the stent.

For the image fusion step, the region of voxels within the 3D dataset is optionally constrained, i.e. voxels which would impair the result of the image fusion are omitted. This restriction of voxels if preferably obtained by applying a threshold similar or equal to the one used for determining the axis of symmetry, optionally in combination with the selection of only the voxels located in a volume within a certain distance from the main axis of the stent and within a certain distance of the center of gravity of the stent. Use of the volume restriction allows the use of a lower threshold without other structures starting to appear in the second (2D or 3D) dataset. A lower threshold is beneficial to make sure that voxels that are only partly filled with stent material (and thus have a smaller apparent density) are also used to render the secondary 2D or 3D dataset.

The method in accordance with the invention is in particular a data processing method. The data processing method is preferably performed using technical means, in particular a computer. The computer comprises in particular a processor and in particular a memory, in order to process the data, in particular electronically. In particular, the calculating steps described are performed by a computer. Steps of defining for example regions or values are in particular steps of determining data within the framework of the technical data processing method, in particular within the framework of a program. Altering steps represent in particular altering the data by means of the computer. Ascertaining steps include in particular retrieving values which are provided at an interface of the computer and have been generated by technical means, such as for example a scanning device. These values are in particular converted by the interface into data which can be processed by the computer.

Another embodiment, which is an independent part of this invention, relates to the general aspect of using a weighting factor or penalty factor in image fusion. This can be used for any application of image fusion, for example for fusing datasets or images containing bones or other (anatomical or non-anatomical) structures. As explained above, image fusion is used to match a first dataset and a second dataset, for example for determining the relative position of the first and second datasets. Image fusion can be applied for up to six degrees of freedom: up to three rotational degrees freedom and up to three translational degrees of freedom. The first and second datasets can be, for example, 2D or 3D datasets, i.e. representing 2D or 3D images. During image fusion, the first dataset is brought into several virtual positions and compared to the second dataset for each virtual position, for example yielding a similarity measure and then choosing the position which results in the highest similarity measure. A virtual position can be a position relative to the position of the second dataset.

In the general method according to this invention, the first and second dataset are provided. Image fusion is performed on these datasets, wherein a virtual starting position of the first dataset is defined and a deviation of the current virtual position under test from this virtual starting position is weighted, for example penalized. Preferably, weighting is performed by applying the weighting factor to the similarity measure, for example dividing the similarity measure by the penalty factor. This weighting or penalizing can be done for one or more degrees of freedom covered by the image fusion, i.e. one or more rotational and/or translational degrees of freedom. The virtual starting position can be derived from prior knowledge, for example of the position of the patient. This prior knowledge might be gained from markers placed on the body of the patient. Such markers or reference adapters are described, for example, in the published patent application US2002/0095081A1 which is hereby incorporated by reference. Such markers and deriving positions from markers are well known in the field of image guided surgery. Preferably, the virtual starting position is equal to or at least close to the most probable actual position of the first dataset.

This general method can be combined with any other applicable feature described in this document. For example, the first dataset in its virtual starting position and the second dataset can be merged and displayed to a user. The user might be given the option to change the virtual starting position. Preferably, the penalty increases with increasing deviation of the current virtual position from the virtual starting position. The penalty can have different characteristics for each dimension, for example be linear, quadratic, exponential or inverse Gaussian.

The general image fusion method can be described by the steps of: providing a first and second dataset; determining a virtual starting position for the first dataset; and performing image fusion on the first and second dataset, thereby weighting a deviation of the current virtual position under test from said virtual starting position.

A second aspect of the present invention relates to a computer program for determining the position of a stent within a body, comprising the program steps of: providing a 3D dataset of voxels representing a 3D image containing a stent; determining a starting position for the determination of the stent position; determining the axis of symmetry of the stent in the 3D dataset; determining a second dataset representing at least one image containing the stent in its present position; and determining the position of the stent by image fusion using the 3D dataset and the second dataset, wherein a rotation around the axis of symmetry versus the starting position is penalized.

This second aspect of the invention relates to a computer program which implements the method as described in the first aspect of the invention. Therefore, the method steps described in the first aspect of the invention can also be implemented as program steps in the computer program of the second aspect of the invention. The method steps are in particular steps of providing and processing data (datasets) by means of a computer. The data (dataset) may be provided by means of a data storage of the computer.

Computer program elements of the invention may be embodied in hardware and/or software (including firmware, resident software, micro-code, etc.). The computer program elements of the invention may take the form of a computer program product which may be embodied by a computer-usable or computer-readable storage medium comprising computer-usable or computer-readable program instructions, "code" or a "computer program" embodied in said medium for use by or in connection with the instruction executing system. Such a system can be a computer; a computer can be a data processing device comprising means for executing the computer program elements and/or the program in accordance with the invention. Within the context of this application, a computer-usable or computer-readable medium may be any medium which can contain, store, communicate, propagate or transport the program for use by or in connection with the instruction executing system, apparatus or device. The computer-usable or computer-readable medium may for example be, but is not limited to, an electronic, magnetic, optical, electromagnetic, infrared or semiconductor system, apparatus, device or medium of propagation, such as for example the Internet. The computer-usable or computer-readable medium could even for example be paper or another suitable medium on which the program is printed, since the program could be electronically captured, for example by optically scanning the paper or other suitable medium, and then compiled, interpreted or otherwise processed in a suitable manner. The computer program product and any software and/or hardware described here form the various means for performing the functions of the invention in the example embodiment(s). The computer and/or data processing device can in particular constitute a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or vibration element incorporated in an instrument).

Where data, regions, ranges or images are "provided", this means that they are ready for use by the method in accordance with the invention. The data, regions, ranges or images can achieve this state of being "provided" for example by being detected or captured (for example by analysis apparatus) or by being inputted (for example via interfaces). The data can also have this state by being stored in a memory (for example a ROM, CD, hard drive) and thus ready for use within the framework of the method in accordance with the invention. The data, regions, ranges or images can also be determined, in particular calculated, in a step of the method before being provided, in particular before being stored.

A third aspect of the present invention relates to a system for determining the position of a stent within a body, comprising: a device for providing a 3D dataset of voxels representing a 3D image containing the stent; a device for determining a starting position for the determination of the stent position; a device for determining the axis of symmetry of the stent in the 3D dataset; a device for providing a second dataset representing at least one image containing the stent in its present position; and a device for determining the position of the stent by image fusion using the 3D dataset and the second dataset, wherein a rotation around the axis of symmetry versus the starting position is penalized.

The device for providing a 3D dataset can for example be a computer tomograph or a magnetic resonance imaging apparatus. The device for providing the second dataset can for example be an x-ray apparatus. The device for determining the starting position, the device for determining the axis of symmetry and the device for determining the position of the stent can for example be computers. In one variant, at least two of these three devices are embodied in a single computer.

Optionally, additional method steps as explained in the first aspect of the present invention can be implemented, either by introducing additional devices or by adapting one or more of the existing devices.

A fourth aspect of the present invention relates to a stent designed to be introduced into a body. In accordance with the present invention, the stent is not rotationally symmetrical about any axis, i.e. there is no axis about which the stent exhibits a rotational symmetry. This means that an image fusion approach will result in the correct position of the stent.

The stent is preferably a one-piece stent, i.e. it is made from a single piece of material. This results in a stent which is easy to produce and reproduce.

The stent is also preferably made of a material having a shape memory. This means that the stent returns to its original shape, preferably subject to a delay, after it has been deformed. This has the advantage that the stent can be deformed for insertion and returns to its original shape once it is in place.

In one example embodiment, the stent is made of at least one coil. Such a stent is easy to produce.

In another example embodiment, the stent has an asymmetrical extension. This extension is used to make a stent which has a symmetrical base body asymmetrical.

In yet another example embodiment, the stent is made of several coils, wherein at least one of the coils is not aligned with the other coils, i.e. not all of the centers of the coils lie on one line. Preferably, at least two of the coils have different diameters.

It is possible to combine features of several of these example embodiments with each other.

A fifth aspect of the present invention relates to a system comprising: a stent which is not rotationally symmetrical about any axis; and an apparatus for determining the position of the stent within a body. The stent can be any stent as described in the fourth aspect of the invention. The apparatus for determining the position of the stent can comprise an image generating device which generates an image of the body, including the stent, and a computer for calculating the position of the stent based on this image, for example using image fusion.

It is possible to omit features of the respective embodiments or aspects and to combine features from different embodiments or aspects, for example by providing devices or designing existing devices such that they can perform method steps.

Figure 2:
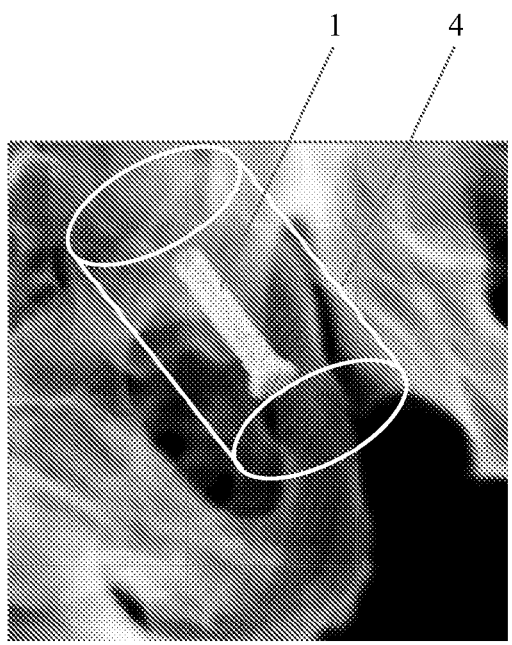
Figure 3:
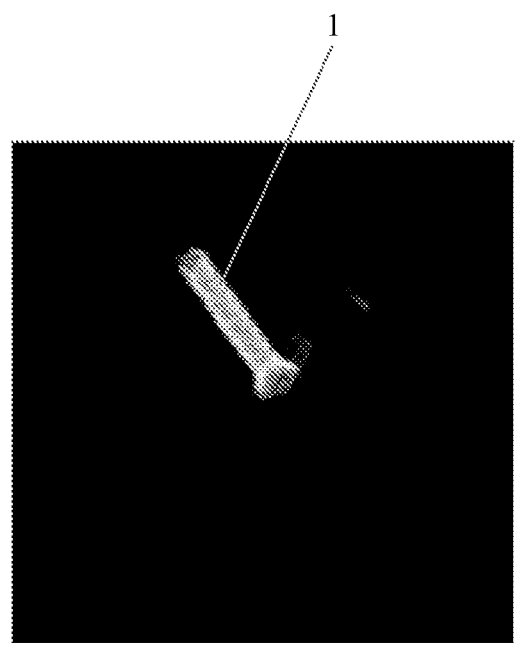
Figure 4:
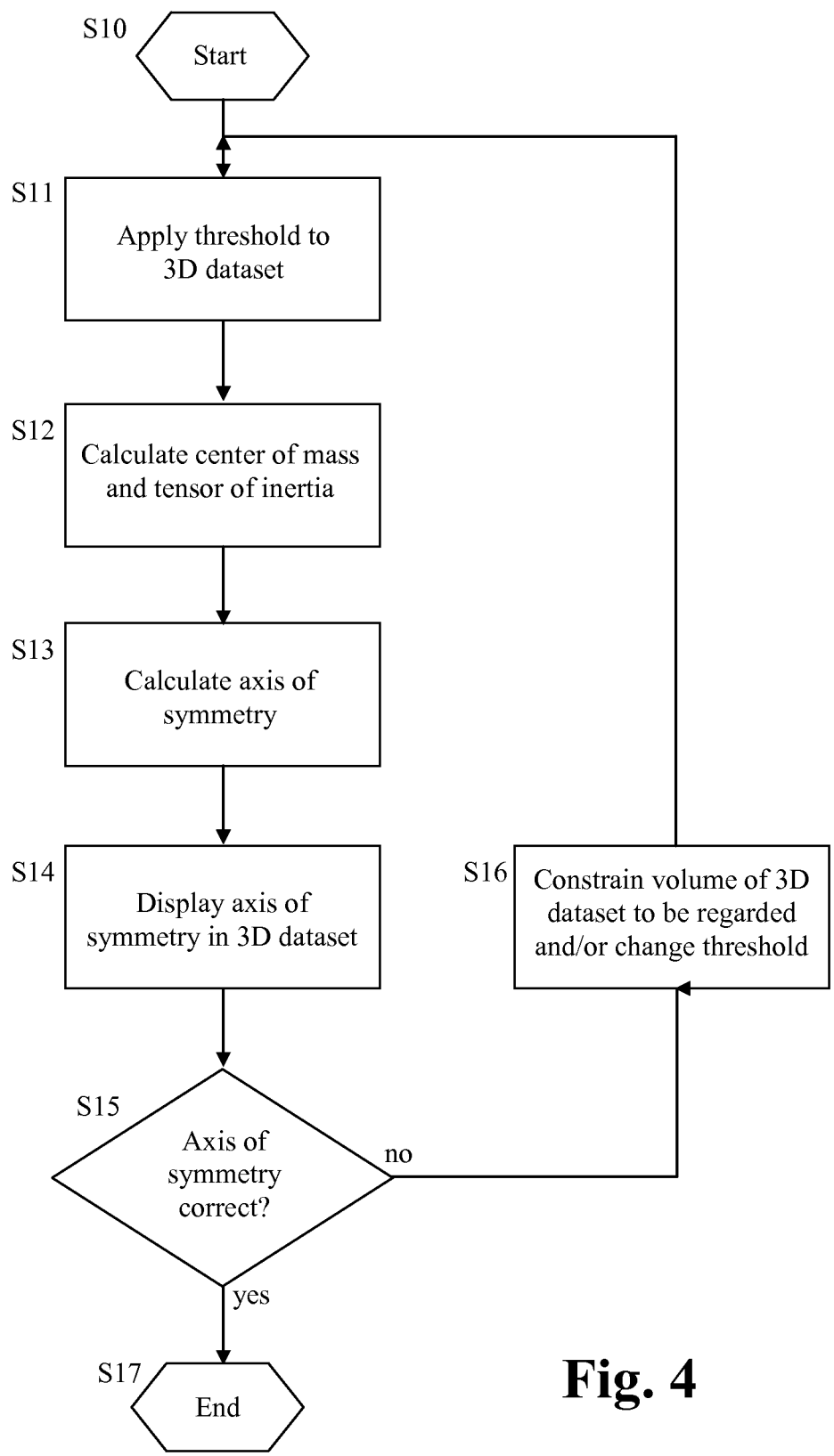
Figure 5:
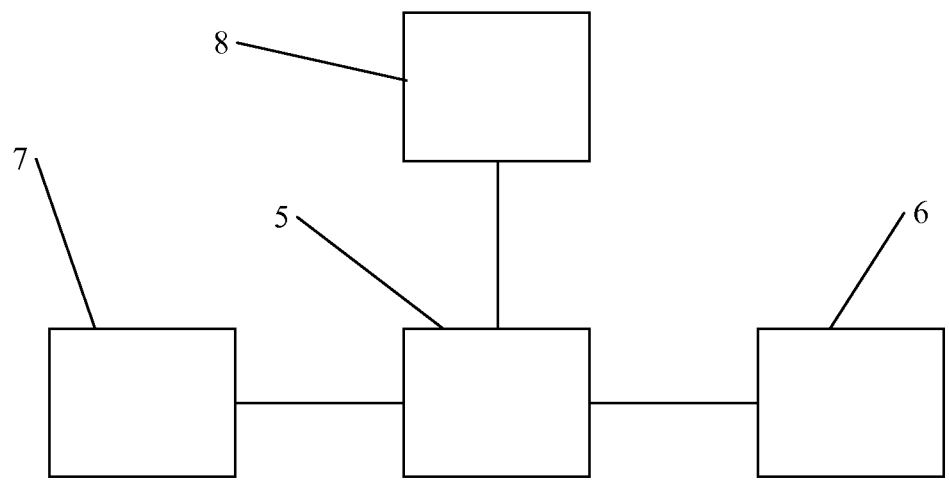
Figure 6:
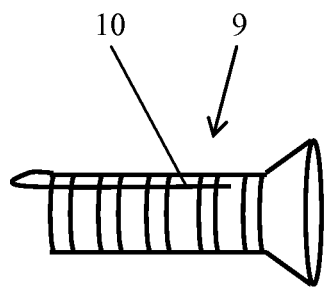
Figure 7:
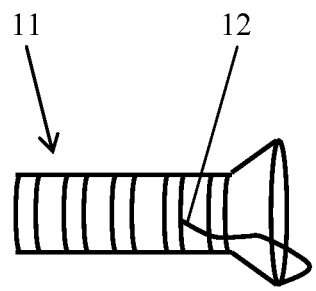
Figure 9:
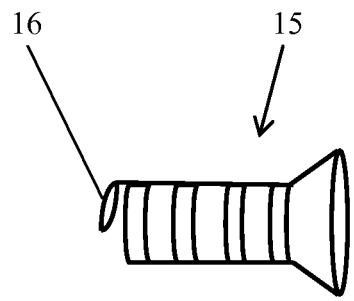

Several example embodiments of the present invention are described below in more detail by referring to the accompanying drawings, which show:

FIG. 1 a section through a 3D image;

FIG. 2 a virtual DRR image;

FIG. 3 a virtual DRR image from a constrained volume;

FIG. 4 a flow chart for determining the axis of symmetry of a stent;

FIG. 5 a system for determining the position of a stent;

FIG. 6 a stent with an asymmetrical extension;

FIG. 7 another stent with an asymmetrical extension;

FIG. 8 a stent made of non-aligned coils;

FIG. 9 a stent made of asymmetrical coils; and

Figure 10:
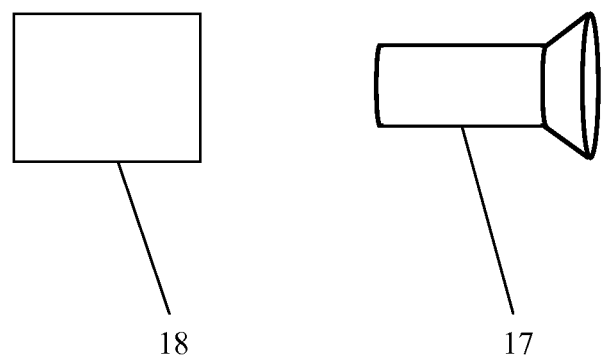

FIG. 10 a system for determining the position of stent.

FIG. 1 shows a section through a 3D image which was recorded using a computer tomograph or a magnetic resonance imaging apparatus. The image shows the contours of a symmetrical metallic stent 1, which is visible as a bright area. The 3D image consists of a multitude of voxels, wherein each voxel is assigned a grey value. This grey value corresponds to the density of the material contained in the volume corresponding to the respective voxel. A high grey value, i.e. a bright voxel, corresponds to a high density of the material, and vice versa. The cross-sectional view in FIG. 1 shows other bright areas, which correspond to bones.

First, the axis of symmetry of the stent 1 is identified in the 3D dataset representing the 3D image. A flow chart comprising the steps for determining the axis of symmetry is shown in FIG. 4. Determination is initiated in step S10. In step S11, a threshold is applied to the voxel values of the 3D dataset. In this step, all voxels above a certain grey value are considered to be part of the stent 1. In a subsequent step S12, the center of mass and the tensor of inertia of the stent 1 are calculated from the thresholded voxels. In the next step S13, the axis of symmetry of the stent 1 is calculated as the tensor's eigenvector associated with the smallest eigenvalue of the tensor.

In a subsequent step S14, the calculated axis of symmetry is displayed within the 3D image, in order to be checked by a user. The axis of symmetry is indicated by the reference sign 3 in FIG. 1. If the user decides in step S15 that the calculated axis of symmetry is not the correct axis of symmetry of the stent 1, then the volume of the 3D dataset from which the stent is detected is constrained and/or the threshold is adapted in step S16 and the method is repeated from step S11. If only the volume is constrained, the method can return directly to step S12 instead of step S11. A possible border for constraining the volume is indicated by the box 2 in FIG. 1.

Calculating the axis of symmetry and therefore detecting the stent may for example fail because the 3D dataset contains other metallic objects (such as piercings, screws or implants). This problem is overcome by step S16. The volume can be constrained automatically or by the user.

Steps S11 to S15 (or S12 to S15, as applicable) are repeated until the axis of symmetry 3 of the stent 1 has been correctly calculated.

A starting position is then determined which is used as a basis for determining the position of the stent 1 in a patient's body. There are several ways of determining the starting position. In the present example, the starting position is determined using external markers.

Markers are placed on the outside of the patient's body. The position of said markers is determined, for example using a medical navigation system known from the prior art. The position of the patient's body can then be derived from the positions of the markers. Since the body opening at which the stent was inserted into the body is known, for example into the prostatic urethra, and since the approximate position of the urethra within the body is known, the approximate position of the stent 1 is also therefore known. This approximate position is then used as the starting position.

At least one x-ray image of the body, specifically of the part of the body containing the stent, is then generated. Based on the at least one x-ray image and the 3D dataset, the position of the stent is determined using image fusion. During image fusion, the 3D model of the stent 1 in the 3D dataset is rotated and/or displaced in steps, and the at least one x-ray image is compared to at least one virtual (DRR) image of the stent 1 in each step. The result of this comparison is a measure of similarity, wherein the measure of similarity increases as the similarity between the DRR image and the x-ray image increases.

The result of image fusion is the position of the stent 1 in which the virtual images and the x-ray images exhibit the best match. However, the result may be an implausible stent position, for example because the patient cannot be in the position which would correspond to the calculated stent position.

In order to avoid such implausible stent positions, a rotation around the axis of symmetry as compared to the starting position of the stent is penalized when determining the stent position. This is achieved by introducing a penalty factor which increases as the rotational deviation around the axis of symmetry from the starting position increases. For example, the penalty factor can be subtracted from the measure of similarity, or the measure of similarity can be divided by the penalty factor. This results in a modified measure of similarity which is generated using image fusion and considers the fact that the actual stent position is likely to be close to the starting position.

For example, if a stent position which deviates from the starting position around the axis of symmetry by 180° is only a slightly better match than a position which only slightly deviates around the axis of symmetry from the starting position, then the latter is the more probable actual position of the stent because it is unlikely that the patient has turned by 180°.

FIG. 2 shows an example virtual (DRR) image containing the stent 1 as well as the surrounding bones and tissue. In order to improve the reliability of image fusion, it is optionally possible to not use all of the 3D dataset to generate the DRR image. In the present example, the DRR image is calculated from a constrained cylindrical volume around the stent 1 only. The cylinder 4 which constrains this volume is chosen such that the cylinder axis matches the calculated axis of symmetry of the stent 1 and such that the height of the cylinder 4 is larger than the length of the stent 1. An example DRR image of the stent 1 as calculated from the constrained volume is shown in FIG. 3.

In a second example, the inventive method is used to align a patient with a radio therapy apparatus, for example to irradiate a tumor. In addition to the stent 1, the 3D dataset also contains the tumor. The 3D dataset, the axis of symmetry of the stent 1 and the second dataset are determined as in the first example. In addition, a nominal position of the 3D dataset is defined, wherein in this nominal position, the isocenter of the 3D dataset is aligned with the isocenter of the radio therapy apparatus. The method is then used to determine the relative position, i.e. the translational and rotational displacement, of the stent 1 within the 3D dataset in the nominal position of the 3D dataset versus the actual position of the stent 1.

In this example, the starting position for the determination of the (relative) stent position is chosen as the position of the stent 1 in the 3D dataset when the 3D dataset is in the nominal position. In practice, this starting position is close to the actual (absolute) position of the stent 1.

Then, image fusion is performed similar to the first example. Measures of similarity are calculated for several virtual positions of the 3D dataset, incorporating a penalty factor which increases with increasing deviation of the virtual position of the 3D dataset from the nominal position around the axis of symmetry of the stent 1. The result of the image fusion step is the translational and rotational displacement of the 3D dataset from its nominal position to a virtual position in which it matches the images represented by the second dataset best. This displacement, or relative position of the stent 1, equals the difference of the actual position and the desired position of the tumor. This displacement information can be used for alignment by moving the body of the patient, moving the radio therapy apparatus, or both.

The method explained in the second example can be used to align any structure within a body with any reference like an apparatus or a reference coordinate system.

FIG. 5 schematically shows a system for determining the position of a stent within a body. The system comprises a computer 5 which is connected to an x-ray apparatus 8 for providing a second dataset representing at least one image containing the stent in its present position, and a device 6 for providing a 3D dataset of voxels representing a 3D image containing the stent. The device 6 is a computer tomograph or a magnetic resonance imaging apparatus. A display 7, for example a liquid crystal display (LCD), is also connected to the computer 5.

The computer 5 represents a device for determining a starting position for the determination of the stent position, a device for determining the axis of symmetry of the stent in the 3D dataset and a device for determining the position of the stent. The computer 5 is capable of performing image fusion and of penalizing a rotation around the axis of symmetry as compared to the starting position.

FIGS. 6 to 9 show several embodiments of stents which are not rotationally symmetrical about any axis. The stent 9 of FIG. 6 and the stent 11 of FIG. 7 are wound from a wire. In order to break their symmetry, one end of the wire is wound back into the stent tube which forms the base body of the stents 9 and 11. The base body of the stents 9 and 11 has a funnel-like shape. In the case of the stent 9, the end 10 of the wire is wound back into the narrow end of the stent, while in the case of the stent 11, the end 12 of the wire is wound back into the wide end of the stent.

Figure 8A:
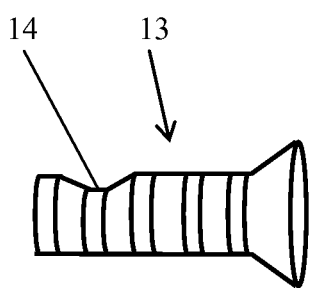
Figure 8B:
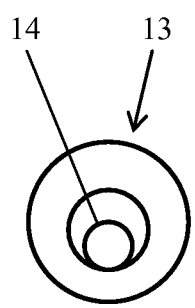

FIG. 8a shows a side view and FIG. 8b an axial view of a stent 13 made of several coils. At least one coil—in the present example, two coils 14—has/have a different diameter to the diameter of the other coils. The coils 14 are not aligned with the other coils, i.e. the center of the coils 14 does not lie on the straight line on which the centers of the other coils lie. Preferably, the coil not aligned with the other coils or having a different diameter to the other coils is not the outermost coil of the coils forming the stent.

FIG. 9 shows a side view of another stent 15 which is formed from several coils and exhibits an asymmetrical placement of coils. The coils form a funnel-like base body of the stent 15. The outermost of the coils—in the present example, the coil 16 at the narrow end of the stent 15—has a different diameter to the other coils and is not aligned with the other coils. In the present example, the coil 16 is also not parallel to the other coils.

FIG. 10 schematically shows a system comprising a stent 17 and an apparatus 18 for determining the position of the stent 17 within a body (not shown). The stent 17 is not rotationally symmetrical about any axis and may be a stent such as has been described with reference to any one or more of FIGS. 6 to 9. The apparatus 18 can be a system such as has been described with reference to FIG. 5.

The example embodiments described above are for illustrative purposes only and are not intended to in any way limit the scope of protection as defined by the appended claims.

The invention claimed is:

1. A method for determining the position of a stent which is placed within a body, comprising the steps of:
   providing a 3D dataset of voxels representing a 3D image containing the stent;
   determining a starting position for the determination of the stent position, wherein the starting position is a position that approximates an actual position of the stent;
   determining the axis of symmetry of the stent in the 3D dataset;
   determining a second dataset representing at least one image containing the stent in its present position; and
   determining the position of the stent by image fusion using the 3D dataset and the second dataset by calculating measures of similarity for different virtual positions of the 3D dataset, wherein the measure of similarity is modified by a penalty factor which increases as the rotation around the axis of symmetry versus a deviation from the starting position increases.

2. The method of claim 1, wherein a nominal position is defined for the 3D dataset and the position of the stent is a relative position versus the stent position in the 3D dataset in the 3D dataset's nominal position.

3. The method of claim 1, wherein a nominal position is defined for the 3D dataset and the starting position for the determination of the stent position is the stent position in the 3D dataset in the 3D dataset's nominal position.

4. The method of claim 1, wherein the starting position is determined from a pre-registration step.

5. The method of claim 1, wherein a nominal position is defined for the 3D dataset and the starting position is determined from the stent position in the 3D dataset in the 3D dataset's nominal position and a pre-registration.

6. The method of claim 1, wherein the axis of symmetry is determined by the steps of:
   applying a threshold for the voxels in the 3D dataset;
   determining the center of mass and the tensor of inertia of the thresholded voxels; and
   calculating the axis of symmetry from the center of mass and the tensor of inertia.

7. The method of claim 3, wherein the axis of symmetry is calculated as the tensor's eigenvector associated with the smallest eigenvalue of the tensor.

8. The method of claim 1, wherein the axis of symmetry is plotted in the 3D dataset, and the 3D dataset is displayed together with the axis of symmetry.

9. The method of claim 1, wherein the region of voxels within the 3D dataset is constrained in order to determine the axis of symmetry of the stent.

10. The method of claim 1, wherein image fusion is performed by x-ray to DRR fusion.

11. The method of claim 1, wherein image fusion is performed by CT to Cone-Beam CT fusion.

12. The method of claim 1, wherein the region of voxels within the 3D dataset is constrained for the image fusion step.

13. The method of claim 1, wherein the starting position is determined as the calculated position of the stent in a previous stent position determination iteration.

14. The method of claim 1, wherein the starting position is determined by performing image fusion based on bone structures.

15. A non-transitory computer readable medium comprising a computer program for determining the position of a stent which is placed within a body, comprising:
   code that provides a 3D dataset of voxels representing a 3D image containing the stent;
   code that determines a starting position for the determination of the stent position, wherein the starting position is a position that approximates an actual position of the stent;
   code that determines the axis of symmetry of the stent in the 3D dataset;
   code that determines a second dataset representing at least one image containing the stent in its present position; and
   code that determines the position of the stent by image fusion using the 3D dataset and the second dataset by calculating measures of similarity for different virtual positions of the 3D dataset, wherein the measure of similarity is modified by a penalty factor which increases as the rotation around the axis of symmetry versus a deviation from the starting position increases.

16. A system for determining the position of a stent which is placed within a body, comprising:
- a device for providing a 3D dataset of voxels representing a 3D image containing the stent;
- a device for determining a starting position for the determination of the stent position, wherein the starting position is a position that approximates an actual position of the stent;
- a device for determining the axis of symmetry of the stent in the 3D dataset;
- a device for providing a second dataset representing at least one image containing the stent in its present position; and
- a device for determining the position of the stent by image fusion using the 3D dataset and the second dataset by calculating measures of similarity for different virtual positions of the 3D dataset, wherein the measure of similarity is modified by a penalty factor which increases as the rotation around the axis of symmetry versus a deviation from the starting position increases.

17. A stent designed to be introduced into a body, characterized in that the stent is not rotationally symmetrical about any axis.

18. The stent of claim 17, wherein the stent is a one-piece stent.

19. The stent of claim 17, wherein the stent is made of a material having a shape memory.

20. The stent of claim 17, wherein the stent is made of at least one coil.

21. The stent of claim 17, wherein the stent has an asymmetrical extension.

22. The stent of claim 17, wherein the stent is made of several coils and at least one of the coils is not aligned with the other coils.

23. The stent of claim 22, wherein at least two of the coils have different diameters.

* * * * *